United States Patent [19]

Inoue

[11] Patent Number: 4,764,018
[45] Date of Patent: Aug. 16, 1988

[54] APPARATUS FOR MEASURING WATER CONTENT

[75] Inventor: Hiroki Inoue, Mishima, Japan
[73] Assignee: EOS Corporation, Mishima, Japan
[21] Appl. No.: 50,478
[22] Filed: May 18, 1987
[51] Int. Cl.⁴ .................................................. G01J 3/51
[52] U.S. Cl. ................................. 356/418; 250/339; 356/419; 356/445
[58] Field of Search ............... 356/416, 418, 419, 445; 250/339, 340

[56] References Cited

U.S. PATENT DOCUMENTS 4,687,335 8/1987 Zupanick et al. ............... 356/419 X Primary Examiner—Vincent P. McGraw
Attorney, Agent, or Firm—Wenderoth, Lind & Ponack

[57] ABSTRACT

An apparatus for measuring the water content of an object to be measured comprises in combination a pair of optical filters for obtaining from the same source light a reference light having a wavelength not easily absorbed therein and a measuring light having a wavelength easily absorbable therein, an optical system for irradiating the object with the reference and measuring lights, an photoelectric converter for converting the reference and measuring lights to electrical signals, a temperature detector for detecting the temperature of the optical filters, a humidity detector for detecting the humidity of optical paths for the reference and measuring lights, extending from the optical system to the object, and a water content-measuring circuit for finding the quantity of water contained in the object on the basis of output signals produced from the photoelectric converter, temperature detector and humidity detector.

1 Claim, 3 Drawing Sheets

APPARATUS FOR MEASURING WATER CONTENT

BACKGROUND OF THE INVENTION

1. Field of the Ivention

The present invention relates to an apparatus for measuring a water content of an object to be measured, wherein the object to be measured is irradiated with a reference light having a wavelength not easily absorbed therein and a measuring light having wavelength easily abosrbable therein, and the quantity of water contained in the object is calculated from the rate of the quantity of the measuring light absorbed therein with respect to the quantity of the reference light absorbed therein, and more particularly to such an apparatus further including a calibration device.

2. Statement of the Prior Art

Hitherto, such an apparatus has been known from Japanese Patent Laid-Open (Kokai) Publication No. 61(1986)-4915, for instance. According to the teachings disclosed therein, reference and measuring lights to strike upon an object, the water content of which is to be measured, are obtained from the same light source through optical filters.

Then, the reference and measuring lights are sent to a photoelectric converter through the object to be measured, and the rate of the quantity of the measuring light absorbed therein with respect to the quantity of the reference light absorbed therein is calculated on the basis on the output signals produced from that converter.

Further, the quantity of water contained in the object to be measured is calculated from the rate of the measuring light absorbed, and is indicated on a display.

When such an apparatus is used for measuring the water content of granular materials such as coal in the open air, the reference and measuring lights are absorbed in moisture present in optical paths, through which the reference and measuring lights pass, due to variations in the humidity thereof.

In consequence, it is impossible to measure the quantity of water contained in the object to be measured with high accuracy.

Another proposal has been made in Japanese Patent Kokai Publication No. 59(1984)-72047 in which the humidity of the aforesaid optical paths is detected to correct the measurement value with the thus detected humidity.

However, there is a change-with-temperature in the characteristics of the optical filters for obtaining from the same light source the reference and measuring lights to strike upon the object, the water content of which is to be measured. Even with such a proposal, therefore, it is impossible to measure, with high accuracy, the quantity of water contained in the object to be measured owing to such temperature dependence.

In the prior art, the correction characteristics of measurements have had to be manually preset by operation of a potentiometer, etc. However, this has been laborious and timeconsuming.

SUMMARY OF THE INVENTION

With the foregoing problems in mind, one object of the present invention is to provide the aforesaid type apparatus which enables constantly accurate measurement irrespective of changes in ambient tempeature.

Another object of the present invention is to provide the aforesaid type apparatus which allows easy and rapid settinghon of the correction characteristics of measurements.

According to the present invention, the aforesaid objects are achieved by the provision of an apparatus for measuring the water content of an object to be measured comprising in combination:

a pair of optical filters for obtaining from the same source light a reference light having a wavelength not easily absorbed in said object and a measuring light having a wavelength easily absorbable in said object;

an optical system for irradiating said object with said reference and measuring lights extracted through said optical filters;

an photoelectric converter for converting said reference and measuring lights incident from said object to electrical signals;

a temperature detector for detecting the temperature of said optical filters;

a humidity detector for detecting the humidity of optical paths for said reference and measuring lights, extending from said optical system to said object; and water content-measuring circuit for finding the quantity of water contained in said object on the basis of output signals produced from said photoelectric converter, said temperature detector and said humidity detector, said water content-measuring circuit including:

means for calculating a temperature correction factor from a linear equation involving as the variable a detected temperature given by the output signal from said temperature detector;

means for calculating a humidity correction factor from a linear equaltion involving as the variable a detected humidity given by the output signal form said humidity detector;

means for calculating the rate of the quantity of said measuring light absorbed in said object with respect to the quantity of said reference light absorbed in said object from a linear equation involving as the variable a value obtained by multiplying the ratio of the intensities of said reference and measuring lights indicated by the output signals from said photoelectric converter by said temperature and humidity correction factors;

means for calculating the quantity of water contained in said object from a linear equation involving as the variable the absorbance of the measuring light calculated; and means for determining the equations for calculating said temperature and humidity correction factors, using the output signals from said temperature and humidity detectors which are obtained under the conditions where both the temperature of said optical filters and the humidity of said optical path are varied.

DETAILED DESCRIPTION OF THE PREFERRED EMBODIMENTS

The present invention will be described by way of examples with reference to the drawings.

Figure 1:
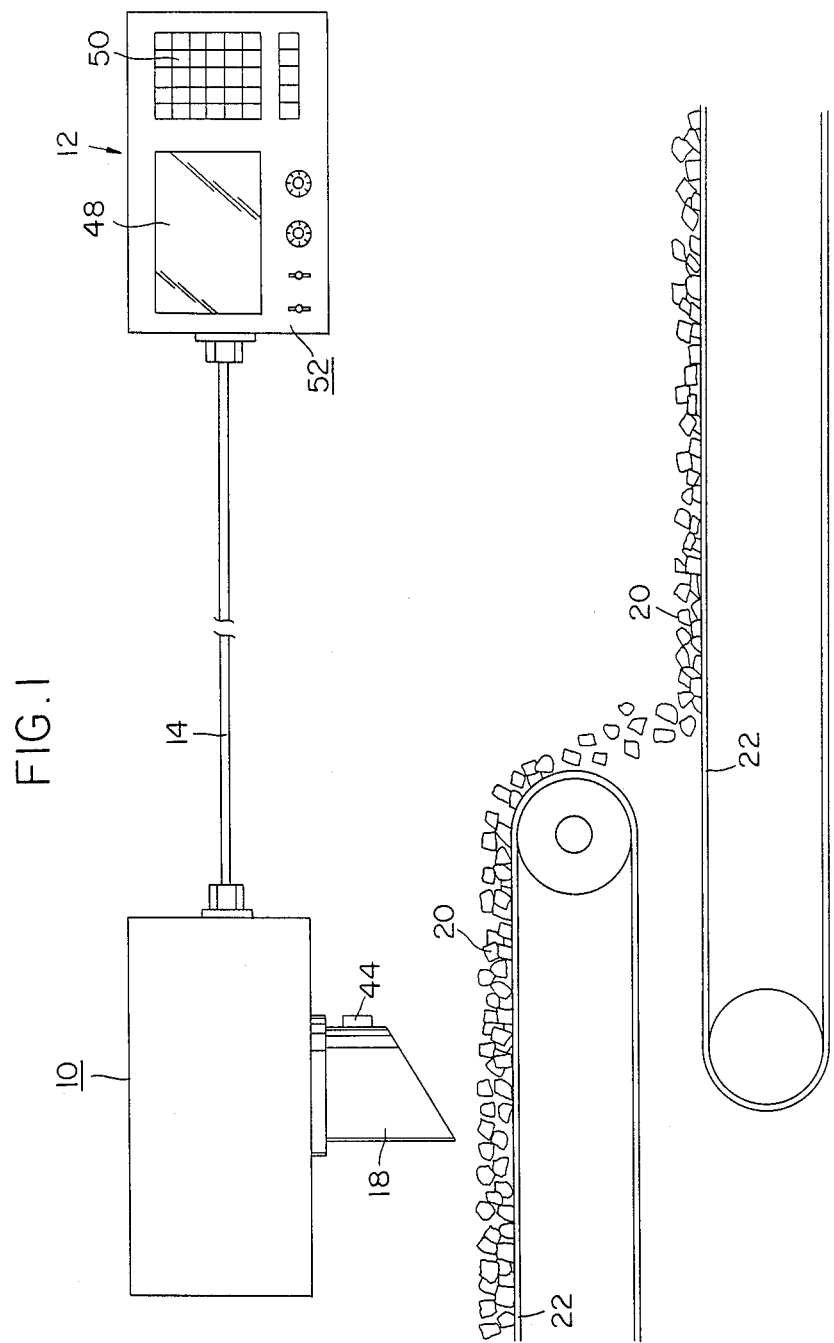
FIG. 1 is a view illustrating the general structure of one preferred embodiment of the present invention.

Referring now to FIG. 1, there is shown one preferred embodiment of the present invention comprising a sensor unit 10 and a measuring unit 12 connected with each other by a cable 14.

The sensor unit 10 includes a casing 16 provided at the lower side with a hood 18 below which granules 20 such as coal granules (the object, the water content of which is to be measured) are carried to the righthand direction on a belt 22.

The quantity of water contained in the granules 20 is measured by the apparatus according to this embodiment. To this end, the granules 20 are irradiated with reference and measuring lights from within the unit 10 through the hood 18.

Figure 2:
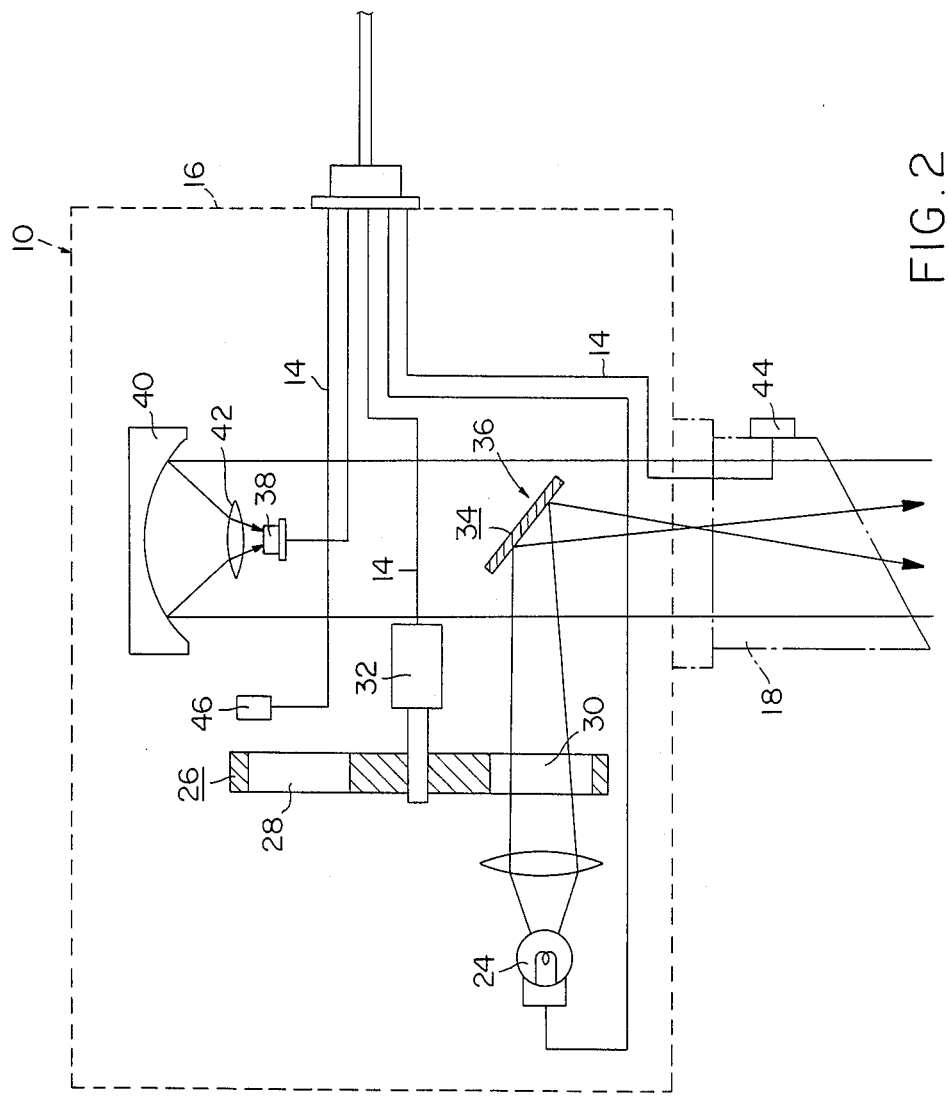
FIG. 2 is a view illustrating the structure of the unit 10.

In the unit 10, as can be seen from FIG. 2, there are a lamp 24 and a rotary disc 26 to which optical filters 28 and 30 are attached. Obtained through the respective filters 28 and 30 from the light source, the lamp 24, are a reference light having a wavelength not easily absorbed in the grunules 20 (i.e., moisture contained therein) and a measuring light having a wavelength easily absorbed in the granules 20.

The disc 26 is driven and rotated by a motor 32, and the reference and measuring lights are allowed to be incident on a mirror 36 forming an optical system 34 through the optical filters 28 and 30.

The reference and measuring lights reflected from that mirror 36 strike alternately upon the granules 20 through the hood 18, are partly absorbed therein, and are received on a photoelectric converter 38 set within the casing 16.

It is understood that the photoelectric converter 38 uses a semiconductor receiver element having a light-receiving surface on which the reference and measuring lights are concentrated through a mirror 40 and a visible-light cut filter 42.

The hood 18 is provided with a humidity detector 44 for detecting the humidity prevailing in paths through which the reference and measuring lights pass.

In the vicinity of the rotary disc 26 to which the optical filters 28 and 30 are attached, there is further a temperature detector 46 for detecting the temperatures thereof.

The lamp 24, motor 32 and humidity and temperature detectors 44 and 46 are connected through the cable 14 to the unit 12, which is provided thereon with a display 48 and a key board 50.

Figure 3:
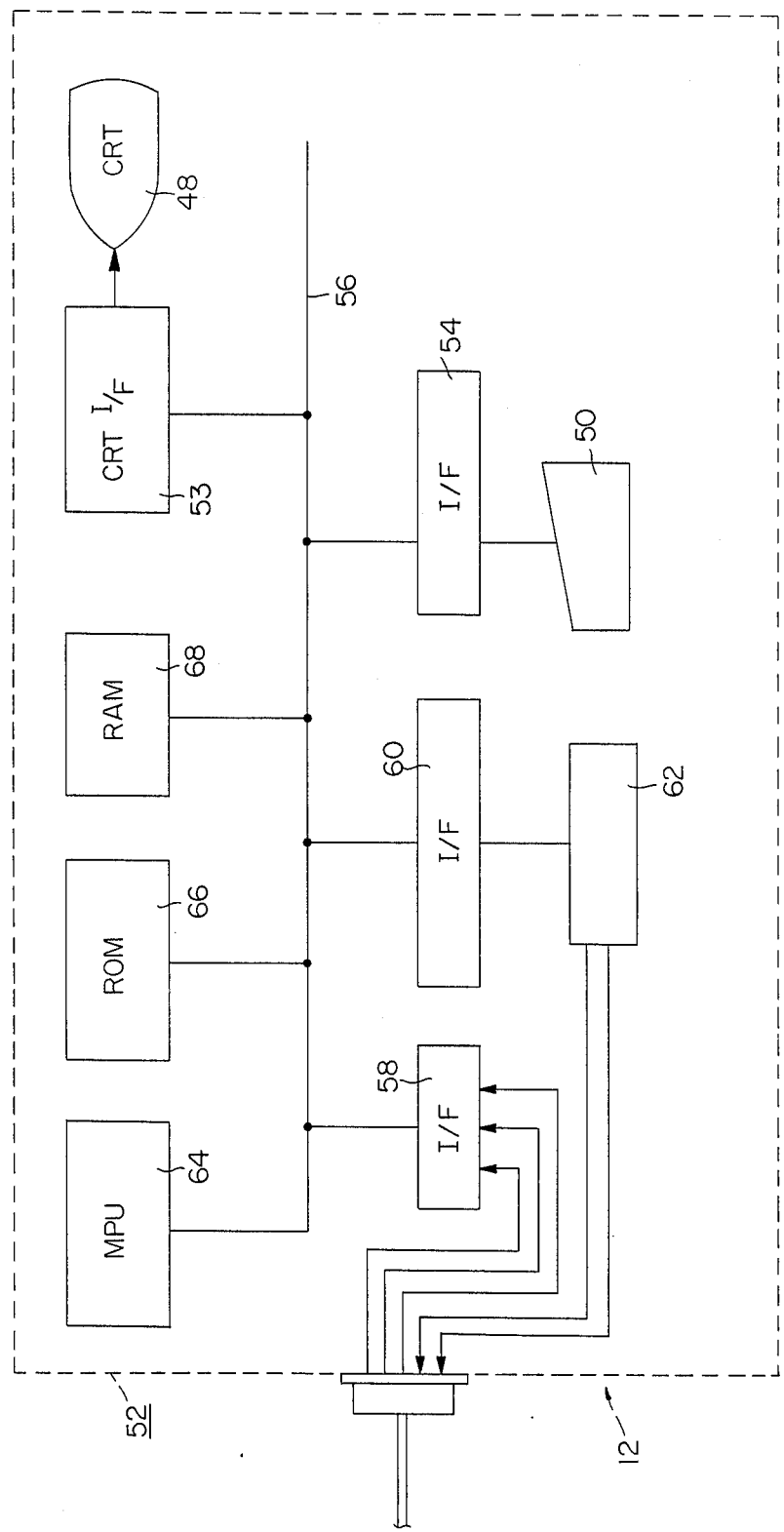
FIG. 3 is a view illustrating the structure of the unit 12.

The display 48 and key board 50 are attached to a casing 52 of the unit 12, and are connected to a bus 56 through respective interfaces 53 and 54, as illustrated in FIG. 3.

Connected to the bus 56 are respectively the lamp 24 and motor 32 through an interface 60 and a driving circuit 62, and the humidity and temperature detectors 44 and 46 through an interface 58.

MPU 64, ROM 66 and RAM 68 are also connected to the bus 56 to calculate measurements in MPU 64, using RAM 68 according to the content of memory stored in ROM 66.

It is also understood that MPU 64 forms a water content-measuring circuit for finding the quantity of water contained in the granules 20 on the basis of the output signals from the photoelectric converter 38 and the temperature and humidity detectors 46 and 44.

The foregoing embodiment operates as follows:

If the quantity in % of water contained in the granules 20 is designated by M, the rate of the measuring light absorbed in the granules 20 with respect to the reference light absorbed therein by X, the offset constant by A and the gradient constant by B, then $M=A+BX$ holds, wherein:

M is as mentioned above,

X is the moisture absorption showing the rate of the measuring light absorbed in the granules 20 with respect to the reference light absorbed therein, A is the offset constant, and B is the gradient constant.

Then, X (the quantity of water in %) is found by:

$$X = a + bx$$

wherein:

x is the variable depending upon the influences of temperature, humidity, etc., a is the offset constant, and b is the gradient constant.

If the intensities of the reference and measuring lights detected are indicated by R and S, respectively, then x (the variable depending upon the influences of temperature, humidity, etc.) is found by:

$$x = ln\{(R/S) \cdot kt \cdot kh\}$$

wherein:

kt is the temperature factor, and kh is the humidity factor.

Further, if the humidity and temperature detected are indicated by Vh and Vt, respectively, then the factors kh and kt are respectively found by:

$$kh = ah + bh \cdot Vh, \text{ and}$$

$$kt = at + bt \cdot Vt$$

respectively.

The condition for which X does not vary in spite of one humidity $Vh_1$ changing to another humidity $Vh_2$ is that both X values found by the aforesaid respective equations are equal at the humidities $Vh_1$ and $Vh_2$. Thus, $$S(Vh_1)/R(Vh_1) \cdot kh(Vh_1) = S(Vh_2) \cdot (kh(Vh_2))$$

holds. Similarly, $$S(Vt_1) \cdot kt(Vt_1) = S(Vt_2) \cdot kt(Vt_2)$$

holds for the condition for which X does not vary in spite of one temperature $Vt_1$ changing to another temperature $Vt_2$.

If $kh(Vh_1)$ and $kt(Vt_1)$ are preset at 1, then $kh(Vh_2)$ and $kt(Vt_2)$ are expressed in terms of:

$$kh(Vh_2) = \{S(Vh_1)/R(Vh_1)\{ \neq \{S(Vh_2)/R(Vh_2)\}, \text{ and}$$

$$kt(Vt_2) = \{S(Vt_1)/R(Vt_1)\{ \neq \{S(Vt_2)/R(Bt_2)\},$$

respectively.

Therefore, if these values are expressed in terms of Nh and Nt, respectively, then $1 = ah + bh \cdot Vh_1$ holds at the one humidity $Vh_1$, whereas $Nh = ah + bh \cdot Vh_2$ holds at the another hudmitity $Vh_2$.

At the one temperature $Vt_1 1 = at + bt \cdot Vt_1$ holds whereas, at the another temperature $Vt_2$, $Nt = at + bt \neq Vt_2$ holds.

In this embodiment, the optical filters for calibration are attached in place prior to the measurment of water contents, and the unit 10 is placed in a tank which can be kept at constant temperature and humidity.

Then, the humidity and temperature of that tank are set at the one humidity $Vh_1$ (=40%) and the one temperature $Vt_1$(=10° C.), respectively.

When a certain period of time elapses afterwards, the detected values $Vh_1$ (=40%) and $Vt_1$(=10° C.) are read in.

Subsequently, the humidity and temperature of that tank are set at the another humidity $Vh_2$ (=70%) and temperature $Vt_2$ (=40° C.), respectively.

When a certain period of time elapses afterwards, the detected values $Vh_2$ (=70%) and temperature $Vt_2$ (=40° C.), respectively.

When a certain period of time elapses afterwards, the detected values $Vh_2$ (=70%) and $Vt_2$ (=40° C.) are read in.

Upon the detected values $Vh_1$ (=40%), $Vt_1$ (=10° C.), $Vh_2$ (=70%) and $Vt_2$ (=40° C.) being read in in this manner, the aforesaid simultaneous equations:

$$1 = ah + bh \cdot Vh_1$$

$$Nh = ah + bh \cdot Vh_2$$

$$1 = at + bt \cdot VT_2$$

$$Nt = at + bt \cdot VT_2$$

are solved to calculate the values ah, bh, at and bt.

Upon finishing of learning of these values, ah, bh, at and bt, it is possible to measure the water content of the granules 20 in the open air.

At this time, the values x, X and M are respectively found by:

$$x = \ln\{(R/S) \cdot kt \cdot kh\},$$

$$X = a + bx, \text{ and}$$

$$M = A + BX,$$

and are indicated on the display 48.

Thus, the present invention makes it possible to carry out constantly accurate measurement irrespective of changes in ambient temperature and humidity.

The present invention also makes it possible to easily and rapidly set the correction characteristics of measurements.

It is understood that while the output signals of the photoelectric converter 38 may be in error due to temperature changes, but such an error is absorbed at the time of learning of the aforesaid factors. Therefore, the accuracy of the measurement M is always maintained irrespective of temperature changes.

Such an error may also be absorbed by electronic feed-back techniques.

What is claimed is

1. An apparatus for measuring the water content of an object to be measured comprising in combination:
    a pair of optical filters for obtaining from the same source light a reference light having a wavelength not easily absorbed in said object and a measuring light having a wavelength easily absorbable in said object;
    an optical system for irradiating said object with said reference and measuring lights extracted through said optical filters;
    an photoelectric converter for converting said reference and measuring lights incident from said object to electrical signals;
    a temperature detector for detecting the temperature of said optical filters;
    a humidity detector for detecting the humidity of optical paths for said reference and measuring lights, extending from said optical system to said object; and
    water content-measuring circuit for finding the quantity of water contained in said object on the basis of output signals produced from said photoelectric converter, said temperature detector and said humidity detector,
    said water content-measuring circuit including:
    means for calculating a temperature correction factor from a linear equation involving as the variable a detected temperature given by the output signal from said temperature detector;
    means for calculating a humidity correction factor from a linear equation involving as the variable a detected humidity given by the output signal form said humidity detector;
    means for calculating the rate of the quantity of said measuring light absorbed in said object with respect to the quantity of said reference light absorbed in said object from a linear equation involving as the variable a value obtained by multiplying the ratio of the intensities of said reference and measuring lights indicated by the output signals from said photoelectric converter by said temperature and humidity correction factors;
    means for calculating the quantity of water contained in said object from a linear equation involving as the variable the absorbance of the measuring light calculated; and
    means for determining the equations for calculating said temperature and humidity correction factors, using the output signals from said temperature and humidity detectors which are obtained under the conditions where both the temperature of said optical filters and the humidity of said optical path are varied.

* * * * *